United States Patent [19]

Wight et al.

[11] 4,228,182

[45] Oct. 14, 1980

[54] IMMUNOSUPPRESSIVE M-FLUORODITHIOCARBANILATES

[75] Inventors: Hewitt G. Wight; Tracey G. Call, both of San Luis Obispo, Calif.; Marvin L. Mortensen, Mesa, Ariz.

[73] Assignee: The California Polytechnic State University Foundation, San Luis Obispo, Calif.

[21] Appl. No.: 52,614

[22] Filed: Jun. 27, 1979

Related U.S. Application Data

[63] Continuation-in-part of Ser. No. 911,600, Jun. 1, 1978, which is a continuation of Ser. No. 848,433, Nov. 4, 1977, Pat. No. 4,130,578, which is a continuation-in-part of Ser. No. 773,064, Feb. 28, 1977, Pat. No. 4,110,444, which is a continuation-in-part of Ser. No. 579,449, May 21, 1975, abandoned.

[51] Int. Cl.$^3$ ............... C07C 153/11; A61K 31/215
[52] U.S. Cl. ..................... 424/300; 260/455 A
[58] Field of Search .................... 260/455 A; 424/300

[56] References Cited

U.S. PATENT DOCUMENTS 3,686,413  8/1972  Hollrah ........................... 424/300

FOREIGN PATENT DOCUMENTS 1153487  5/1969  United Kingdom ................ 424/300

Primary Examiner—Henry R. Jiles
Assistant Examiner—Robert C. Whittenbaugh
Attorney, Agent, or Firm—Robert A. Armitage

[57] ABSTRACT

The present invention to certain immunosuppressive ω-(alkoxycarbonyl)alkyl m-fluorodithiocarbanilates. These compounds surprisingly and unexpectedly exhibit useful immunosuppressive effects in the treatment of tissue transplantation rejection phenomena and are useful in the symptomatic treatment of autoimmune diseases.

5 Claims, No Drawings

IMMUNOSUPPRESSIVE M-FLUORODITHIOCARBANILATES

CROSS REFERENCE TO RELATED APPLICATIONS

The present application is a continuation-in-part of U.S. Ser. No. 911,600, filed June 1, 1978, now pending; which is a continuation application of U.S. Ser. No. 848,433, filed Nov. 4, 1977, now U.S. Pat. No. 4,130,578, issued Dec. 19, 1978; which is a continuation-in-part of Ser. No. 773,064, filed Feb. 28, 1977, now U.S. Pat. No. 4,110,444, issued Aug. 29, 1978; which is a continuation-in-part of Ser. No. 579,449, filed May 21, 1975, now abandoned.

TECHNICAL FIELD

The present invention relates to novel organic compounds which surprisingly exhibit pronounced immunosuppressive effects.

Particularly provided by the present invention are certain immunosuppressive m-fluorodithiocarbanilates, compounds whose preparation and pharmacological use is described in U.S. Pat. No. 4,130,578, issued Nov. 4, 1977, the essential material constituting a disclosure of the preparation and immunosuppressive use of such m-fluorodithiocarbanilates is incorporated here by reference.

PRIOR ART

Meta-substituted dithiocarbanilates other than m-fluorodithiocarbanilates are known in the art. Such compounds are described in British Pat. No. 1,153,487 and U.S. Pat. No. 3,686,413.

SUMMARY OF THE INVENTION

The present invention particularly comprises:
(a) a compound of the formula I
wherein T is nitro, fluoro, chloro, bromo, trifluoromethyl, lower alkylsulphonyl, phenylsulphonyl, or (lower alkyl)phenylsulphonyl;
wherein s is the integer zero or one;
wherein $C_mH_{2m}$ is alkylene of one to 5 carbon atoms, inclusive; and
wherein $R_2$ is alkyl of one to 12 carbon atoms, inclusive;
(b) a compound of formula II
wherein $C_mH_{2m}$ is alkylene of one to 5 carbon atoms, inclusive; and
wherein $R_2$ is alkyl of one to 12 carbon atoms, inclusive;
(c) a compound of formula III
wherein $R_2$ is alkyl of one to 12 carbon atoms, inclusive; and
(d) a compound of formula IV
wherein $R_{12}$ is alkyl of one to 2 carbon atoms, inclusive.

An especially important species of the present invention is ω-(methoxycarbonyl)ethyl m-fluorodithiocarbanilate.

The preparation and use of the compounds set forth above is incorporated here by reference from U.S. Pat. No. 4,130,578.

As indicated in U.S. Pat. No. 4,130,578, the compounds of the instant invention are all highly active as immunosuppressive agents.

The immunosuppressive effects of this compound are most apparent in their ability to prolong survival time of allografts, i.e., organ or tissue transplants from genetically distinct organisms of the same species, and are further manifest by the ability of the pharmaceutical agents of the instant invention to symptomatically treat certain hyperimmunity diseases, i.e., diseases where excesses within the immune system cause ontoward physiological effects.

The compounds of the instant invention assert their immunosuppressive effects in part by suppressing the cytotoxicity or cell-killing ability of certain lymphocytes, e.g. T-effector cells. For a brief review of the constituent components and actions of the immune systems, see Wechter, W. J., et al., Progress is Drug Research 20:573 (1976).

In mammalian species T-effector cells are known to function as cytotoxic or cell-killing agents in the destruction of foreign cells. In an allograft, those foreign cells, although from the same species, are recognized as being genetically distinct. In hyperimmunity diseases, the body becomes sensitized against certain of its own tissues and acts to destroy these tissues in the same manner as if they were foreign to that body. Suppression of such T-effector cells would, therefore, result in the effective prolonging or allograft survival time or symptomatically improving a hyperimmunity disease.

The ability of the compounds of the instant invention to function as suppressors of the cytotoxicity of the T-effector cells, and thus exert the desirable immunosuppressive effects referred to above, is measured by standard laboratory means.

One important such means of assessing these immunosuppressive effects is by a radioactive chromium ($^{51}Cr$) release assay known in the art. For a description of the rationale and operation of this chromium release assay, see Bruner, K. T., et al., "Quantitative Assay of Lytic Action of Immune Lymphoid Cells on $^{51}$Cr-labbelled Allogeneic Target Cells in Vitro; Inhibition of Isoantibody and by Drugs", Immunology 14:188–196 (1968) and Henney, C. S., J. Immunol. 107:1558 (1971). By one standard embodiment of this chromium release assay P815 mouse mastocytoma cells are introduced into DBA/2 mice where an ascites tumor forms. After incubation, the ascites tumor is removed from the peritoneal cavity by withdrawal into a syringe containing about 5 ml of sterile EDTA-sucrose (anti-coagulant solution). The resulting suspension is then centrifuged and resuspended in RPMI-1640 or HEPES buffer and 10% heat-inactivated calf serum (56° C. for 30 min), the diluent or assay medium used throughout.

The suspended mastocytoma cells are then used for the following purposes:

(a) Radiolabelling. $^{51}$Cr-labelled sodium chromate ($Na_2CrO_4$) of greater than 200 curies per gram chromium is employed at a rate of 100 μcuries per $5 \times 10^6$ cells. Labelling is accomplished by incubating the P815 cells as prepared above and the radiolabelled sodium chromate at 37° C. for 30 min followed by a washing (5 times in the assay medium, RPMI-1640 with HEPES buffer supplemented with 10% serum). 1 ml of each washed supernatant is then collected and assayed for radio-activity, which at first decreases and then stabilizes with succeeding washes. Total radioactivity is then estimated by making a microscopic viable cell count on a known volume of the final suspension, followed by a radioactivity count of the same sample. The number of disintegrations, corrected for dilution, is an accurate estimate of the total radioactivity expected in each assay.

(b) Lymphocyte production. C51B1/6 mice are used as a source of sensitized or cytotoxic T-effector cells and normal lymphocytes. Sensitization is accomplished by innoculation of the mice with $50-60 \times 10^6$ mastocytoma cells. At least three mice are so sensitized and the spleens therefrom harvested, pooled, and mixed to a single cell suspension. After washing, the cells are resuspended in the assay medium above.

Assays are then performed in $10 \times 75$ mm glass tubes. The ratio of lymphocyte to target cells is 50:1, with lymphocytes being present at initial concentrations in diluent of $1 \times 10^7$ per ml of assay medium and target cells at $2 \times 10^5$ per ml of assay medium. Test runs contain lymphocytes (sensitized T-effector cells), target cells (mastocytoma cells), drug, and assay medium. Control tubes are used wherein an equal volume of diluent or assay medium is substituted for a drug. Drugs are prepared at 500, 50 and 5 mg per ml, yielding 100, 10, and 1 mg per ml final concentrations. Next sensitized T-effector cells (0.10 ml at $1 \times 10^7$ cells per ml) and target cells (0.10 ml) are added.

In order to determine total radioactivity per tube, tubes are innoculated with 0.10 ml each of target cell suspension, to which is added 1.9 ml distilled water. These are incubated and corked until asay determination. All tubes are incubated at 37° C. which are then flushed with nitrogen, carbon dioxide and oxygen. When the assay is terminated, the tubes are removed form the incubation chamber and centrifuged at 1500 RPM for 10 minutes. 1 ml is then removed from each H$_2$O lysis tube (described above) and transferred to glass tubes for counting. The tubes are stoppered with corks prior to placement in a gamma counter. At this time the previously corked tubes (above) are centrifuged and 0.5 ml of supernatant is collected. All counts are then corrected to specific values by subtraction of counts attributable to nonspecific lysis, determined from tubes containing normal lymphocytes, target cells, and drug.

Results obtained by the assay are as follows:

(a) Percentage specific lysis for drug-containing tubes (SL-D), which is the ratio of radioactivity released into the assay medium from activated T-effector cell and drug-containing tubes to the total releasable radioactivity on complete target cell lysis in H$_2$ (both corrected for radioactivity resultant from lysis of target cell by normal lymphocytes in drug-containing solutions), expressed as a percentage.

(b) Percentage reduction from control (PR-C), which is the ratio, expressed as a percent, of SL-D to the ratio of radioactivity released into the assay medium, the specific lysis for control (no drug-sensitized T-effector cells) tubes to the total releasable radioactivity (measured as for SL-D), both figures being corrected for radioactivity resultant from lysis of target cells by normal lymphocytes in drug-containing solutions.

(c) Percent immunosuppression (P-I), which is the percentage by which the drug at 100 mg/ml has reduced from control the ability of the T-effector cells to lyse the target cells, which is 100 (PR-C).

Compounds are considered active when the P-I is at least 70% at highest concentration tested.

The novel compounds of the instant invention being alkyl esters of carboxylic acids are hydrolyzable in vivo to the corresponding carboxylic acids by tissue esterases in the course of the exertion of their immunosuppressive effects. Unless and until hydrolysis occurs the novel esters of the instant invention do not demonstrate appreciable immunosuppressive activity. For the purposes of evaluating the immunosuppressive effects of the novel esters in the chromium release assay, the corresponding free acids are employed in place of the esters, since these acids represent the active in vivo form of the novel esters and the in vitro test conditions result in inactivation of serum esterases capable of hydrolysis. When the free acid or salt form of a novel compound of the instant invention, ω-(methoxycarbonyl)ethyl m-fluorodithiocarbanilate, is tested against the free acid forms of corresponding prior art m-chloro- and m-bromo-substituted dithiocarbanilates, the results reported in Table I are obtained. The results establish that the free acid and salts corresponding to the novel ω-(alkoxycarbonyl)ethyl m-fluorodithiocarbanilates are all surprisingly and unexpectedly immunosuppressive, while corresponding prior art m-chloro- and m-bromo-substituted compounds exhibit no measurable degree of immunosuppressive activity.

DESCRIPTION OF THE PREFERRED EMBODIMENTS

The preferred compound for accomplishing the immunosuppressive effects described above is ω-(methoxycarbonyl)ethyl m-fluorodithiocarbanilate.

| IMMUNOSUPPRESSIVE EFFECTS OF FREE ACID AND SALT FORMS OF ω-(ALKOXYCARBONYL)ETHYL DITHIOCARBANILATES SUBSTITUTED IN THE META POSITION BY FLUORO, CHLORO, OR BROMO | | | | | | | | |
|---|---|---|---|---|---|---|---|---|
| | SL | | | PR-C | | | | |
| Compound | 100 | 10 | 1 | 100 | 10 | 1 | P-I | Comment |
| ω-(hydroxycarbonyl)-ethyl m-fluorodithiocarbanilate | — | 25 | 32 | — | 78 | 100 | — | Active |
| ω-(hydroxycarbonyl)-ethyl m-fluorodithiocarbanilate | 4 | 34 | 39 | 10 | 100 | 115 | 90 | Active |
| ω-(hydroxycarbonyl)-ethyl m-fluorodithiocarbanilate | 10 | 35 | 46 | 23 | 82 | 108 | 77 | Active |
| ω-(hydroxycarbonyl)-ethyl m-fluorodithiocarbanilate, sodium salt | 4 | 37 | 39 | 10 | 97 | 104 | 90 | Active |
| ω-(hydroxycarbonyl)-ethyl m-fluorodithiocarbanilate, | — | 25 | 30 | — | 83 | 100 | — | Active |

IMMUNOSUPPRESSIVE EFFECTS OF FREE ACID AND SALT FORMS OF ω-(ALKOXYCARBONYL)ETHYL DITHIOCARBANILATES SUBSTITUTED IN THE META POSITION BY FLUORO, CHLORO, OR BROMO

| Compound | SL 100 | SL 10 | SL 1 | PR-C 100 | PR-C 10 | PR-C 1 | P-I | Comment |
|---|---|---|---|---|---|---|---|---|
| sodium salt ω-(hydroxycarbonyl)-ethyl m-chlorodithiocarbanilate | 17 | 32 | 52 | 57 | 106 | 140 | 43 | Inactive |
| ω-(hydroxycarbonyl)-ethyl m-chlorodithiocarbanilate | 25 | 41 | 60 | 58 | 95 | 140 | 42 | Inactive |
| ω-(hydroxycarbonyl)-ethyl-m-bromodithiocarbanilate | 32 | 39 | 36 | 107 | 130 | 120 | (7) | Inactive |
| ω-(hydroxycarbonyl)-ethyl-m-bromodithiocarbanilate | 37 | 43 | 43 | 86 | 100 | 100 | 14 | Inactive |

FORMULAS

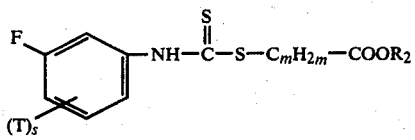

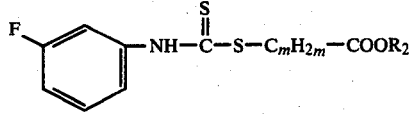

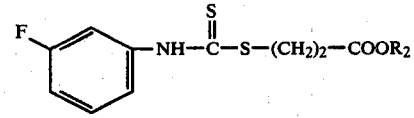

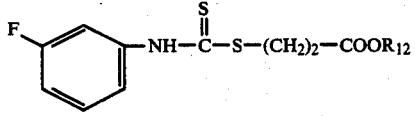

We claim:

1. A compound of the formula

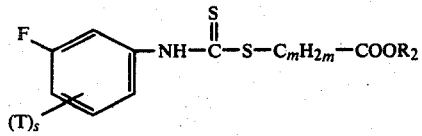

wherein T is nitro, fluoro, chloro, bromo, trifluoromethyl, lower alkylsulphonyl, phenylsulphonyl, or (lower alkyl)phenylsulphonyl;
wherein s is the integer zero or one;
wherein $C_mH_{2m}$ is alkylene of one to 5 carbon atoms, inclusive; and
wherein $R_2$ is alkyl of one to 12 carbon atoms, inclusive;

2. A compound of the formula

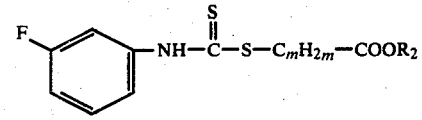

wherein $C_mH_{2m}$ is alkylene of one to 5 carbon atoms, inclusive; and
wherein $R_2$ is alkyl of one to 12 carbon atoms, inclusive;

3. A compound of the formula

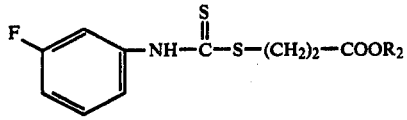

wherein $R_2$ is alkyl of one to 12 carbon atoms, inclusive; and

4. A compound of the formula

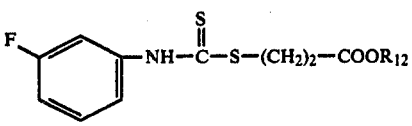

wherein $R_{12}$ is alkyl of one to 2 carbon atoms, inclusive.

5. ω-(Methoxycarbonyl)ethyl m-fluorodithiocarbanilate, a compound according to claim 4.

UNITED STATES PATENT OFFICE
CERTIFICATE OF CORRECTION

Patent No. 4,228,182                    Dated 14 October 1980

Inventor(s) H. G. Wight, et al.

It is certified that error appears in the above-identified patent and that said Letters Patent are hereby corrected as shown below:

Column 3, line 27, "asay" should read -- assay --.

Column 3, line 31, "form" should read -- from --.

Column 6, line 55, "inclusive; and" should read -- inclusive. --

Column 5, line 23, insert -- (I) --; line 28, insert -- (II) --; line 32, insert -- (III) --; and line 37, insert -- (IV) --.

*Signed and Sealed this*

*Tenth* Day of *March 1981*

[SEAL]

*Attest:*

RENE D. TEGTMEYER

*Attesting Officer*     *Acting Commissioner of Patents and Trademar*